United States Patent [19]

Schmid et al.

[11] Patent Number: 5,759,979
[45] Date of Patent: Jun. 2, 1998

[54] DETERGENT MIXTURES COMPRISING APG AND FATTY ALCOHOL POLYGLYCOL ETHER

[75] Inventors: Karl Schmid, Mettmann; Brigitte Giesen; Karin Koren, both of Duesseldorf, all of Germany

[73] Assignee: Henkel Kommanditgesellschaft auf Aktien

[21] Appl. No.: 535,266

[22] PCT Filed: Apr. 5, 1993

[86] PCT No.: PCT/EP94/00975

§ 371 Date: Oct. 4, 1995

§ 102(e) Date: Oct. 4, 1995

[87] PCT Pub. No.: WO94/22997

PCT Pub. Date: Oct. 13, 1994

[30] Foreign Application Priority Data

Apr. 5, 1993 [DE] Germany .............. 43 11 114.9

[51] Int. Cl.⁶ .............. C11D 3/22; C11D 1/722; C11D 1/94
[52] U.S. Cl. .............. 510/237; 510/235; 510/413; 510/422; 510/424; 510/470; 510/490; 510/494; 510/506; 510/535; 510/537
[58] Field of Search .............. 510/470, 506, 510/235, 237, 340, 356, 421, 422, 490, 413, 535, 537, 424, 494

[56] References Cited

U.S. PATENT DOCUMENTS

| 4,240,921 | 12/1980 | Kaniecki | 252/156 |
|---|---|---|---|
| 4,732,704 | 3/1988 | Biermann et al. | 252/548 |
| 4,965,014 | 10/1990 | Jeschke et al. | 510/376 |
| 5,370,816 | 12/1994 | Salzer et al. | 510/340 |
| 5,374,716 | 12/1994 | Biermann et al. | 536/18.6 |

FOREIGN PATENT DOCUMENTS

| 0075996 | 4/1983 | European Pat. Off. |
| 0070075 | 1/1987 | European Pat. Off. |
| 0070076 | 1/1987 | European Pat. Off. |
| 0070077 | 1/1987 | European Pat. Off. |
| 0070074 | 6/1988 | European Pat. Off. |
| 0301298 | 2/1989 | European Pat. Off. |
| 0408965 | 1/1991 | European Pat. Off. |
| 3534082 | 4/1987 | Germany |
| 4039223 | 6/1992 | Germany |
| 4124247 | 1/1993 | Germany |
| 4237178 | 5/1994 | Germany |
| 2194536 | 3/1988 | United Kingdom |
| 2242686 | 10/1991 | United Kingdom |
| 80039777 | 4/1990 | WIPO |
| 9114760 | 10/1991 | WIPO |
| 9220768 | 11/1992 | WIPO |

OTHER PUBLICATIONS

Tens. Surf. Det. 28, 413 (1991).
Falbe (ed.) "Surfactants in Consumer Products", Springer–Verlag, 1986, pp. 114–119.
Fette, Seifen, Anstrichmitt., 74, 163 (1972).

*Primary Examiner*—Ardith Hertzog
*Attorney, Agent, or Firm*—Wayne C. Jaeschke; John E. Drach; Henry E. Millson, Jr.

[57] ABSTRACT

Detergent mixtures containing a) alkyl and/or alkenyl oligoglycosides corresponding to formula (I)

$$R^1O-[G]_p \qquad (I)$$

in which $R^1$ is an alkyl or alkenyl radical containing 8 to 22 carbon atoms, G is a sugar unit containing 5 or 6 carbon atoms and p is a number of 1 to 10; b) fatty alcohol polyglycol ethers corresponding to formula (II)

$$R^2O-(CH_2\overset{\underset{\displaystyle CH_3}{|}}{C}HO)_n(CH_2CH_2O)_mH \qquad (II)$$

in which $R^2$ represents alkyl radicals containing 6 to 14 carbon atoms, n is a number of 0.5 to 2 and m is a number of 2 to 10 and, optionally, c) amphoteric or zwitterionic surfactants and water, have synergistic effects in regard to their washing, dishwashing, foaming and cleaning performance and in regard to their skin-cosmetic compatibility. Accordingly, they are suitable for the production of a number of surface-active preparations, particularly manual dishwashing detergents.

6 Claims, No Drawings

DETERGENT MIXTURES COMPRISING APG AND FATTY ALCOHOL POLYGLYCOL ETHER

BACKGROUND OF THE INVENTION

1. Field of the Invention

This invention relates to detergent mixtures containing alkyl and/or alkenyl oligoglycosides, selected fatty alcohol polyglycol ethers and, optionally, amphoteric or zwitterionic surfactants and also water, to manual dishwashing detergents containing these mixtures and to the use of the mixtures for the production of surface-active preparations.

2. Statement of Related Art

Alkyl oligoglycosides and, in particular, alkyl oligoglucosides are nonionic surfactants which, by virtue of their native raw material base (fatty alcohol and sugar), are acquiring increasing significance and are used, for example, in manual dishwashing detergents or cosmetic products [cf. Tens. Surf. Det. 28, 413 (1991)]. However, despite good performance results, there is still a need for detergent mixtures based on alkyl glucosides of which the performance level synergistically exceeds that of the individual components.

There has hitherto been no shortage of attempts to develop detergent mixtures based on alkyl oligoglucosides which have advantageous properties.

EP-B-0 070 074, EP-B-0 070 075, EP-B-0 070 076 and BP-B-0 070 077 (Procter & Gamble), for example, describe high-foaming combinations of alkyl oligoglucosides with anionic surfactants, such as soaps, alkylbenzene sulfonates, fatty alcohol sulfates, conventional fatty alcohol ether sulfates, α-olefin sulfonates and alkane sulfonates and, optionally, betaine surfactants.

According to the teaching of EP-B1 0 075 996 (Procter & Gamble), aqueous cleaning preparations may contain alkyl polyglucosides, fatty alcohol polyglycol ethers and detergent builders. A similar composition is also claimed in DE-A1 40 39 223 (Hüls).

In addition, DE-A1 35 34 082 proposes skin-friendly dishwashing detergents containing a combination of anionic sulfate or sulfonate surfactants, alkyl oligoglucosides and fatty acid alkanolamides.

However, where these known detergent mixtures are used in surface-active preparations, reductions in performance and ecotoxicological compatibility have hitherto had to be accepted in some cases.

Accordingly, the problem addressed by the present invention was to develop detergent mixtures based on alkyl and/or alkenyl oligoglycosides which would have further improved properties.

Above all, a particular concern was to provide concentrates which
- would have a high active substance content,
- would be liquid or at least flowable,
- would have a low cold cloud point,
- would be dermatologically safe, i.e. would not irritate the skin, even in concentrated form and
- at the same time would show high dishwashing power.

DESCRIPTION OF THE INVENTION

The present invention relates to detergent mixtures containing a) alkyl and/or alkenyl oligoglycosides corresponding to formula (I)

$$R^1O\text{—}[G]_p \quad (I)$$

in which $R^1$ is an alkyl or alkenyl radical containing 8 to 22 carbon atoms, G is a sugar unit containing 5 or 6 carbon atoms and p is a number of 1 to 10;

b) fatty alcohol polyglycol ethers corresponding to formula (II)

$$R^2O\text{—}(CH_2CHO)_n(CH_2CH_2O)_mH \quad (II)$$
$$\overset{|}{\underset{}{CH_3}}$$

in which $R^2$ represents alkyl radicals containing 6 to 14 carbon atoms, n is a number of 0.5 to 2 and m is a number of 2 to 10 and, optionally, c) amphoteric or zwitterionic surfactants and water.

It has surprisingly been found that the detergent mixtures according to the invention have a washing, dishwashing, foaming and cleaning power and skin-cosmetic compatibility which exceed those of the individual constituents through synergistic enhancement. At the same time, the mixtures are liquid or flowable, even in highly concentrated form, and have cold cloud points below −3° C. Although mixtures of alkyl oligoglucosides, fatty alcohol polyglycol ethers and betaines are also known in principle from the prior art for the claimed application, the detergent mixtures according to the invention still cannot be regarded as obvious because the claimed combination effect of particular skin-cosmetic compatibility, good cleaning performance and advantageous rheology can only be found in a very small number of the broad range of commercially available fatty alcohol polyglycol ethers; the choice made in accordance with the invention is documented by Comparison Examples.

Starting materials

Alkyl and/or alkenyl oligoglycosides (APG) are known substances which may be obtained by the relevant methods of preparative organic chemistry. EP-A1-0 301 298 and WO 90/3977 are cited as representative of the extensive literature available on the subject.

The alkyl and/or alkenyl oligoglycosides may be derived from aldoses or ketoses containing 5 or 6 carbon atoms, preferably from glucose. Accordingly, the preferred alkyl and/or alkenyl oligoglycosides are alkyl and/or alkenyl oligoglucosides.

The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycpsodes having an average degree of oligomerization p of 1.1 to 3.0 are preferably used. Alkyl and/or alkenyl oligoglycosides having a degree of oligomerization below 1.7 and, more particularly, between 1.2 and 1.4 are preferred from the performance point of view.

Detergent mixtures which combine particularly advantageous cleaning performance with optimal dermatological compatibility are obtained by suitably combining short-chain and relatively long-chain alkyl and/or alkenyl oligoglycosides, but especially alkyl oligoglucosides. Component a) preferably consists of a1) alkyl oligoglucosides corresponding to formula (III)

$$R^3O\text{—}[G]_{p1} \quad (III)$$

in which $R^3$ represents alkyl radicals containing 12 to 16 carbon atoms, G is a glucose unit and p1 is a number of 1 to 3, and a2) alkyl oligoglucosides corresponding to formula (IV)

$$R^4O\text{—}[G]_{p2} \quad (IV)$$

in which $R^4$ represents alkyl radicals containing 8 to 11 carbon atoms, G is a glucose unit and p2 is a number of 1 to 3, the ratio by weight of a1) to a2) being in the range from 1:2 to 2:1 and preferably in the range from 1:0 to 1:1.

The alkyl radical $R^3$ may be derived from primary alcohols containing 12 to 16 carbon atoms. Typical examples are lauryl alcohol, myristyl alcohol and cetyl alcohol and technical mixtures thereof which may be obtained as described above. Alkyl oligoglucosides based on hydrogenated $C_{12/16}$ coconut oil fatty alcohol having a DP of 1 to 3 are preferred.

The alkyl radical $R^4$ may be derived from primary alcohols containing 8 to 10 carbon atoms. Typical examples are caproic alcohol, caprylic alcohol and capric alcohol and undecyl alcohol and also technical mixtures thereof such as are formed, for example, in the hydrogenation of technical fatty acid methyl esters or in the hydrogenation of aldehydes from Roelen's oxo synthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight $C_{12}$ alcohol as an impurity, and alkyl oligoglucosides based on technical $C_{9/11}$ oxoalcohols (DP=1 to 3) are preferred.

The fatty alcohol polyglycol ethers to be used in accordance with the invention are adducts of propylene oxide and ethylene oxide with short-chain fatty alcohols. Typical examples are adducts of, on average, 0.5 to 2 mol propylene oxide and 2 to 10 mol ethylene oxide with caproic alcohol, caprylic alcohol, capric alcohol, lauryl alcohol and myristyl alcohol and technical mixtures thereof such as are formed, for example, in the high-pressure hydrogenation of technical coconut oil or palm kernel oil fatty acid methyl ester fractions. Fatty alcohol polyglycol ethers corresponding to formula (II), in which $R^2$ is an alkyl radical containing 8 to 12 carbon atoms, n is a number of 1 to 1.5 and m is a number of 5 to 9, are preferably used. The products may have a conventional or narrow-range homolog distribution. Fatty alcohol polyglycol ethers which have an internal polypropylene glycol block and a terminal polyethylene glycol block and in which the ratio of EO to PO in the molecule is 2:1 or higher, are also preferred from the performance point of view.

Suitable amphoteric or zwitterionic surfactants are, for example, alkyl betaines, alkyl amidobetaines, aminopropionates, aminoglycinates, imidazolinium betaines and/or sulfobetaines.

Typical examples are the reaction products of fatty amines, fatty acid amides, fatty acid aminoamines or fatty alkyl imidazolines with sodium chloroacetate, acrylates or chlorohydroxypropane sulfonic acid. Particulars of the production and structure of the compounds mentioned can be found in Falbe (ed.), "Surfactants in Consumer Products", Springer-Verlag, 1986, pages 114–119. Alkyl amidobetaines obtained by condensation of technical $C_{8/14}$ coconut oil fatty acid with dimethylaminopropyl amine and subsequent reaction with sodium chloroacetate are preferably used.

Detergent mixtures

Aqueous detergent mixtures distinguished by particularly advantageous performance properties contain

| | |
|---|---|
| 15 to 80 (20 to 50) | % by weight of component a) |
| 20 to 50 (40 to 50) | % by weight of component b), |
| 0 to 30 (20 to 25) | % by weight of component c) and |
| 0 to 40 | % by weight water, | with the proviso that the percentages add up to 100% by weight; the particularly preferred concentration ranges are shown in brackets. As mentioned above, the detergent mixtures may have a solids content of 60 to 100% by weight. However, mixtures having particularly advantageous flow properties are obtained in the range from 65 to 70% by weight solids.

As described above, the following detergent mixtures, in which component a) consists of short-chain and relatively long-chain alkyl oligoglucosides:

| | |
|---|---|
| 10 to 80 (25 to 70) | % by weight of component a1), |
| 5 to 40 (15 to 20) | % by weight of component a2), |
| 20 to 50 (30 to 40) | % by weight of component b), |
| 0 to 30 (20 to 25) | % by weight of component c) and |
| 0 to 40 | % by weight water, | have proved to be particularly advantageous, again with the proviso that the percentages add up to 100% by weight; the particularly preferred concentration ranges are again shown in brackets.

The detergent mixtures may be produced by simple mechanical mixing of the starting materials, optionally at elevated temperatures of 30° to 50° C.; no chemical reaction takes place during the mixing process.

Manual dishwashing detergents

The present invention also relates to manual dishwashing detergents containing a) alkyl and/or alkenyl oligoglycosides corresponding to formula (I)

$$R^1O\text{—}[G]_p \quad (I)$$

in which $R^1$ is an alkyl or alkenyl radical containing 8 to 22 carbon atoms, G is a sugar unit containing 5 or 6 carbon atoms and p is a number of 1 to 10;

b) fatty alcohol polyglycol ethers corresponding to formula (II)

$$R^2O\text{—}(CH_2CHO)_n(CH_2CH_2O)_mH \atop {\displaystyle \overset{|}{CH_3}} \quad (II)$$

in which $R^2$ represents alkyl radicals containing 6 to 14 carbon atoms, n is a number of 0.5 to 2 and m is a number of 2 to 10 and, optionally, c) amphoteric or zwitterionic surfactants and water.

In addition to the detergent mixtures mentioned, the manual dishwashing detergents according to the invention may contain other typical ingredients, for example other anionic, nonionic or amphoteric or zwitterionic co-surfactants, foam boosters, fragrances, etc. A particularly high-performance formulation extremely compatible with the skin may contain, for example, 18% by weight $C_{12/16}$ APG, 10% by weight $C_{8/10}$ APG, 26% by weight octanol-1.2PO-9EO adduct and 18% by weight alkyl amidobetaine (water ad 100% by weight). The manual dishwashing detergents may have a solids content of 15 to 50% by weight and preferably 20 to 40% by weight.

Industrial Applications

The detergent mixtures according to the invention are distinguished by excellent washing, dishwashing and cleaning power and by advantageous skin-cosmetic and ecotoxicological compatibility.

Accordingly, the present invention also relates to their use for the production of laundry detergents, dishwashing detergents and cleaning products and also hair-care and personal hygiene products in which they may be present in quantities of 1 to 50% by weight and preferably 10 to 30% by weight, based on the preparation as a whole.

The following Examples are intended to illustrate the invention without limiting it in any way.

EXAMPLES

I. Surfactants used

A1. $C_{12/16}$ coconut oil alkyl oligoglucoside Plantaren® APG 600 CS UP (50% by weight AS in water);
A2. $C_{8/10}$ alkyl oligoglucoside Plantaren®APG 225 CS UP (68% by weight AS in water);
B1. Octanol-1.2PO-9EO-adduct;
B2. Octanol-1.2-PO-adduct;
B3. Octanol-9EO-adduct;
B4. $C_{12/14}$ coconut oil fatty alcohol 7EO adduct;
C1. Betaine surfactant based on $C_{12/14}$ coconut oil fatty acid amide Dehyton® K, freeze-dried.

All the surfactants used are commercial products of Henkel KGaA, Dusseldorf/FRG. Substances B1 to B4 and C1 are anhydrous.

Formulations containing the fatty alcohol polyglycol ether B1 correspond to the invention. Formulations containing fatty alcohol polyglycol ethers B2 to B4 are comparison formulations.

II. Evaluation of dishwashing performance (DWP)

Dishwashing performance was determined by the saucer test [Fette, Seifen, Anstrichmitt., 74, 163 (1972)]. To this end, saucers 14 cm in diameter were each soiled with 2 cm³ beef tallow (acid value 9–10) and stored for 24 h at room temperature. The saucers were then rinsed at 50° C. with 5 liters tapwater having hardness of 16° d. The test mixture was used in a dosage of 0.15 g active substance/l. The dishwashing test was terminated when the foam had completely disappeared. The results of the dishwashing tests, expressed as the number of clean saucers (CS), are set out in Table 1:

TABLE 1

| | Dishwashing power The formulations contain 28% by weight water | | | | | | | | |
|---|---|---|---|---|---|---|---|---|---|
| | Composition (% by weight) | | | | | | | CS | CCP |
| Ex. | A1 | A2 | B1 | B2 | B3 | B4 | C1 | No. | °C. |
| 1 | 24 | — | 48 | — | — | — | — | 11/8 | <−3 |
| 2 | 18 | — | 36 | — | — | — | 18 | 12/9 | <−3 |
| 3 | 24 | 12 | 36 | — | — | — | — | 12/10 | <−3 |
| 4 | 18 | 10 | 26 | — | — | — | 18 | 13/10 | <−3 |
| C1 | 24 | — | — | 48 | — | — | — | 8/6 | 0 |
| C2 | 24 | — | — | — | 48 | — | — | 8/6 | −1 |
| C3 | 24 | — | — | — | — | 48 | — | 8/6 | −1 |
| C4 | 54 | — | — | — | — | — | 18 | 8/6 | −1 |
| C5 | 18 | — | — | 36 | — | — | 18 | 9/7 | −1 |
| C6 | 18 | 10 | — | 26 | — | — | 18 | 9/7 | −2 |

Legend:
CS = Number of clean saucers grease-free/with specks
CCP = Cold cloud point

What is claimed is:

1. A water-containing manual dishwashing detergent mixture comprising:
(a) (i) an alkyl oligoglycoside of the formula (III)

$$R^3O\text{—}(G)_{p1} \qquad (III)$$

wherein $R^3$ is an alkyl radical having from about 12 to about 16 carbon atoms, G is a glucose unit and p1 is a number of 1 to 3; and
(ii) an alkyl oligoglycoside of the formula (IV)

$$R^4O\text{—}(G)_{p2} \qquad (IV)$$

wherein $R^4$ is an alkyl radical having from about 8 to about 11 carbon atoms, G is a glucose unit and p2 is a number of 1 to 3, wherein the weight ratio of (i) to (ii) is from 1:2 to 2:1; (b) a fatty alcohol polyglycol ether of the formula (II)

$$R^2O\text{—}(CH_2\overset{\underset{\displaystyle CH_3}{|}}{C}HO)_n(CH_2CH_2O)_mH \qquad (II)$$

wherein $R^2$ is an alkyl or alkenyl radical having from about 6 to about 14 carbon atoms, n is a number of 0.5 to 2 and m is a number of 2 to 10; (c) at least one of an amphoteric or zwitterionic surfactant; and (d) water.

2. The detergent mixture of claim 1 wherein $R^2$ is a $C_{8-12}$ alkyl radical, n is a number of 1 to 1.5 and m is a number of 5 to 9.

3. The detergent mixture of claim 1 wherein said at least one amphoteric or zwitterionic surfactant is selected from the group consisting of an alkyl betaine, an alkyl amidobetaine, an aminopropionate, an aminoglycinate, an imidazolinium betaine and a sulfobetaine.

4. The detergent mixture of claim 1 wherein component (a) is present in from about 15 to about 50% by weight, component (b) is present in from about 20 to about 50% by weight, and component (c) is present in from about 20 to about 30% by weight, with the remainder water.

5. The detergent mixture of claim 4 wherein the detergent mixture has a total solids content of from about 60 to about 70% by weight.

6. The detergent mixture of claim 5 wherein the solids content is from about 65 to about 70% by weight.

* * * * *